(12) United States Patent
Martin et al.

(10) Patent No.: US 8,415,390 B2
(45) Date of Patent: Apr. 9, 2013

(54) METHODS AND COMPOSITIONS FOR ADMINISTRATION OF OXYBUTYNIN

(75) Inventors: Michael J. Martin, Chatham, NJ (US); Alan B. Watts, Plainsboro, NJ (US); Robert Cook, Hillsborough, NJ (US)

(73) Assignee: Microdose Therapeutx, Inc., Monmouth Junction, NJ (US)

( * ) Notice: Subject to any disclaimer, the term of this patent is extended or adjusted under 35 U.S.C. 154(b) by 120 days.

(21) Appl. No.: 12/904,964

(22) Filed: Oct. 14, 2010

(65) Prior Publication Data

US 2011/0253133 A1 Oct. 20, 2011

Related U.S. Application Data

(63) Continuation-in-part of application No. 12/130,903, filed on May 30, 2008, now abandoned.

(51) Int. Cl.
*A61K 31/24* (2006.01)
*A61K 9/14* (2006.01)

(52) U.S. Cl. .......................... 514/534; 424/400

(58) Field of Classification Search .................. None
See application file for complete search history.

(56) References Cited

U.S. PATENT DOCUMENTS

| | | | | |
|---|---|---|---|---|
| 5,171,744 A | | 12/1992 | Cross et al. ............... 514/305 |
| 5,532,278 A | * | 7/1996 | Aberg et al. ............... 514/617 |
| 5,677,346 A | | 10/1997 | Aberg et al. ............... 51/617 |
| 5,736,577 A | | 4/1998 | Aberg et al. ............... 514/617 |
| 6,026,809 A | * | 2/2000 | Abrams et al. ........... 128/203.15 |
| 6,183,782 B1 | * | 2/2001 | Hallworth ................. 424/497 |
| 6,254,882 B1 | * | 7/2001 | Jerussi ...................... 424/449 |
| 6,294,582 B1 | * | 9/2001 | Jerussi ...................... 514/617 |
| 2005/0026909 A1 | * | 2/2005 | Landau et al. ............. 514/218 |
| 2005/0087189 A1 | | 4/2005 | Crockford et al. |
| 2007/0060652 A1 | | 3/2007 | Fraser et al. |

FOREIGN PATENT DOCUMENTS

| | | |
|---|---|---|
| WO | WO 00/71108 | 11/2000 |
| WO | WO 03/039464 | 5/2003 |
| WO | WO 2004/039763 | 5/2004 |
| WO | WO 2006/047427 | 5/2006 |

OTHER PUBLICATIONS

Supplementary European Search Report and Search Opinion, dated May 10, 2010, (7 pgs).
Davila et al., "A Short-Term, Multicenter, Randomized Double-Blind Dose Titration Study of the Efficacy and Anticholinergic Side Effects of Transdermal Compared to Immediate Release Oral Oxybutynin Treatment of Patients with Urge Urinary Incontinence," The Journal of Urology, vol. 166, 140-145, Jul. 2001.
Oki et al., "Advantages for Transdermal over Oral Oxybutynin to Treat Overactive Bladder: Muscarinic Receptor Binding, Plasma Drug Concentration, and Salivary Secretion," The Journal of Pharmacology and Experimental Therapeutics, vol. 316, No. 3, pp. 1137-1145, 2006.
Staskin, David R., "Transdermal Systems for Overactive Bladder: Principles and Practice," Reviews in Urology, vol. 5, Suppl. 8, pp. S26-S30, 2003.
U.S. Official Action dated in related U.S. Appl. No. 12/130,903 dated Jun. 3, 2011 (8 pgs).
Australian Patent Examination Report No. 1, Patent Appln. No. 2008259864, dated Nov. 19, 2012 (4 pgs).

* cited by examiner

*Primary Examiner* — Blessing Fubara
*Assistant Examiner* — Jennifer Berrios
(74) *Attorney, Agent, or Firm* — Hayes Soloway P.C.

(57) ABSTRACT

Administration of Oxybutynin directly to a patient's lungs for treating urinary incontinence, respiratory disease or IBD.

12 Claims, 4 Drawing Sheets

METHODS AND COMPOSITIONS FOR ADMINISTRATION OF OXYBUTYNIN

CROSS REFERENCE TO RELATED APPLICATION

This application is a continuation in part of application Ser. No. 12/130,903, filed May 30, 2008 now abandoned.

BACKGROUND OF THE INVENTION

1. Field of the Invention

The present invention relates generally to a novel method of administering Oxybutynin, and to novel forms of Oxybutynin and novel dosage forms containing Oxybutynin adapted for pulmonary route. The invention will be described in particular in connection with pulmonary delivery of Oxybutynin for treatment of respiratory diseases such as asthma and chronic obstructive pulmonary disease (COPD), although other uses such as prophylactic, therapeutic or ameliorative treatment of incontinence and intestinal hypermotility, i.e. irritable bowel syndrome, also are contemplated.

2. Description of the Prior Art

Oxybutynin is a racemic compound of the chemical formula 4-diethylaminobut-2-butynyl phenylcyclohexyl-glycolate:

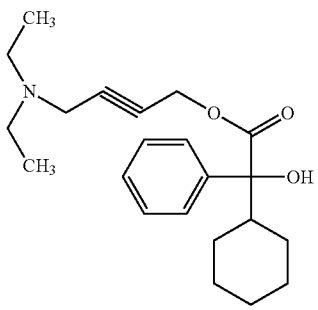 [SMILES: CCN(CC)CC#CCOC(=O)C(O)(c1ccccc1)C1CCCCC1]

Oxybutynin is an anticholinergic medication that traditionally has been used to treat urinary incontinence, urge incontinence, frequency and over-active bladder symptoms of incontinence (hereinafter singly and collectively referred to as "urge urinary incontinence"). Oxybutynin acts by decreasing muscle spasms of the bladder. It competitively antagonizes the M1, M2, and M3 subtypes of the muscarinic acetylcholine receptor. It also has weaker direct spasmolytic effects on bladder smooth muscle as a calcium antagonist and local anesthetic, but at concentrations far above those used clinically. It is available orally in generic formulation and as the chloride salt, and as the brand-names Ditropan® and Ditropan XL®, and as a transdermal patch under the brand-name Oxytrol®.

Oxybutynin currently is administered in oral formulation as a tablet or multiple tablets and a syrup, or transdermally as a patch or topical gel for treating urge urinary incontinence. However, oral delivery of a therapeutically active amount of Oxybutynin suffers from a number of disadvantages:

(1) Oxybutynin administered in an oral formulation is absorbed from the intestinal track at an undesirably slow and uneven rate with a variable metabolism that leads to undesirable variations in blood levels and undesirably high dosage rates to achieve a therapeutic response leading to undesirable side effects;

(2) Oxybutynin administered in an oral formulation does not produce desirably high blood levels in a desirably short period of time;

(3) Oxybutynin administered in an oral formation may result in a significant amount not reaching targeted tissues because it is being wasted by metabolism or excretion;

(4) Oxybutynin administered in an oral formation is contraindicated for patients with gastrointestinal obstruction disorders because of the risk of urinary retention; and (5) Oxybutynin administered in oral formulation requires chronic dosing with significant and severe side effects, including dry mouth (xerostomia), constipation, mydriasis, blurred vision, drowsiness, nausea, palpitations, tachycardia and dizziness.

(6) Oxybutynin administered in the oral formulation is subject to first pass metabolism, resulting in the formation of metabolite N-desethyloxybutynin (DEO) which has been attributed to cause the majority of the aforementioned side effects.

As a result, many patients discontinue oral anticholinergic therapy. These adverse effects have been associated with relatively high levels of Oxybutynin's primary metabolite, DEO, which circulates in concentrations approximately 4 (Oxybutynin ER) to 10 (Oxybutynin IR) times that of the parent compound. DEO has been shown to have an greater affinity and binding duration at receptors in the salivary glands than does Oxybutynin. In other words, the metabolite DEO has shown to have a higher side effect-to efficacy ratio than the parent compound Oxybutynin. Levels of DEO in oral and transdermal therapy have been reported to be approximately 10-40 ng/mL and 3 ng/mL, respectively. To completely eliminate the side effect concerns of this drug, it would be advantageous to decrease the DEO levels in systemic circulation to below those found in current therapies (i.e. below 3 ng/mL).

Moreover, there are other disadvantages to current oral administration of Oxybutynin, including:

(7) Oxybutynin administered in an oral formation is administered as a tablet or multiple tablets which may lack the desirable ease of administration because some people may dislike the swallowing of tablets, or may have difficulty swallowing tablets, or are unable to swallow tablets, or may require a liquid to assist swallowing of tablets; and (8) Oxybutynin-containing tablets also contain several inactive ingredients, including significant amounts of lactose, corn starch, magnesium silicate, magnesium stearate, and talc which may be considered undesirable because some people may dislike or be allergic to one or more of these inactive ingredients that comprise the Oxybutynin tablets.

Transdermal delivery of Oxybutynin has many of the aforesaid disadvantages. Additionally, some patients suffer skin irritation from transdermal patches, have difficulty maintaining and tolerating patch-to-skin contact, or dislike the aesthetics of a transdermal patch.

Thus, there is a need for improved delivery of Oxybutynin, which will provide enhanced bioavailability, minimized variations in blood levels, and achieve more rapid onset of activity, as compared to oral dosage or transdermal dosage forms, while at the same time providing relative ease of administration and reduced side effects compared to current oral and transdermal delivery methods for administering Oxybutynin.

SUMMARY OF THE INVENTION

The foregoing and other objects of the invention are achieved by providing methods and compositions for pulmonary delivery of Oxybutynin to a mammalian host, particularly a human patient, whereby to provide for rapid absorption of Oxybutynin while avoiding the above and other disadvantages of oral and transdermal administration.

More particularly, it has been discovered that Oxybutynin-containing compositions can be usefully administered to mammals by pulmonary delivery at lower dosage levels to elicit a therapeutic response with a marked reduction in systemic metabolites. It is well known to those skilled in the art that the major contributor to the untoward effects of Oxybutynin therapy is systemic levels of the metabolite, DEO. An increased contribution of DEO toward side effects is due to its greater affinity toward receptors in non-targeted tissues, i.e. salivary glands. In addition, this invention can provide enhanced bioavailability, achieve more rapid onset of activity, and ease of administration, as compared to conventional oral and transdermal methods of administration, for treating urinary incontinence. Pulmonary delivery of Oxybutynin provides relief for treating respiratory diseases such as asthma and chronic obstructive pulmonary disease (COPD), as well as relief for treating both urinary incontinence and for treating stress urinary incontinence, as well as intestinal hypermotility, i.e. irritable bowel syndrome. The present invention also provides novel forms of Oxybutynin as well as novel dosage forms and treatment protocols for administering Oxybutynin.

BRIEF DESCRIPTION OF THE DRAWINGS

Further features and advantages of the present invention will be seen from the following detailed description, taken in conjunction with accompanying drawings, in which FIG. 1 plots inhibition of methacholine induced bronchoconstriction of Oxybutynin and Oxybutynin salts at 18 hours.

DETAILED DESCRIPTION OF PREFERRED EMBODIMENTS

Figure 1:
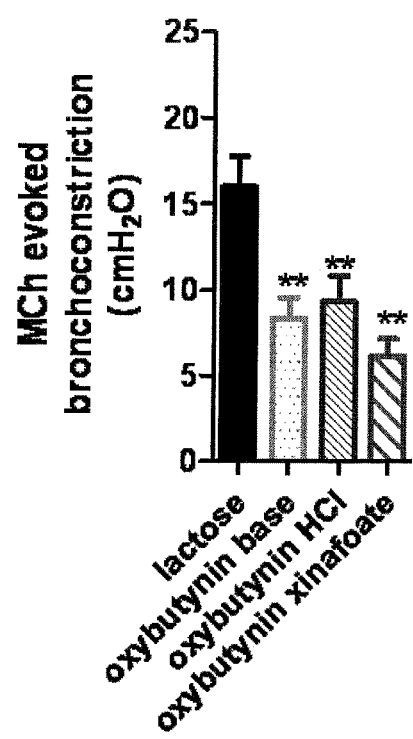

As used herein, the term "Oxybutynin" is intended to encompass not only Oxybutynin as an anhydrous powder, but any salt or derivative of Oxybutynin having antispasmodic, anticholinergic activity like Oxybutynin, and which is non-toxic and pharmacologically acceptable, for example, Oxybutynin hydrochloride or Oxybutynin xinafoate. Other suitable salts include the palmitate, pamoic, resonate and laurate salts.

"An effective amount," as used herein, is an amount of the pharmaceutical composition that is effective for treating urinary incontinence or irritable bowel syndrome, or pulmonary disease, i.e., an amount of Oxybutynin of a defined aerodynamic particle size suitable for absorption in the lungs, that is able to reduce or eliminate the symptoms of urinary and stress incontinence, asthma and COPD.

"A pharmaceutical composition," as used herein, means a medicament for use in treating a mammal that comprises Oxybutynin in a dry powder form of a defined aerodynamic particle size prepared in a manner that is suitable for pulmonary administration to a mammal. A pharmaceutical composition according to the invention may also, but does not of necessity, include a non-toxic pharmaceutically acceptable carrier.

"A defined aerodynamic particle size," as used herein, means particles having a size sufficiently small so as to be delivered to the lungs. For optimal delivery to the lungs, the dry powder form of the Oxybutynin preferably should be micronized or spray dried to a mass median aerodynamic diameter powder size of 0.1-10 microns, preferably 0.5-6 microns. However, other methods for producing controlled size particles, e.g. supercritical fluid processes, controlled precipitation, etc., also advantageously may be employed.

"A therapeutically effective amount" as used herein will vary with the age, weight and general physical condition of the individual, frequency of dosing, severity of incontinence, and whether urge or stress incontinence, irritable bowel syndrome, or asthma or COPD is being treated. Generally, for treating urge incontinence, a therapeutically effective amount will comprise the active ingredient in a quantity of from 1 to 20 mg/day, preferably 1 to 10 mg/day. The active ingredient may be given once a day. Preferably, however, the active ingredient will be administered in smaller doses two or three or more times a day to maintain more consistent plasma levels. When used for treating stress incontinence, or irritable bowel syndrome, a therapeutically amount will comprise the active ingredient in a quantity of from 0.1 to 15 mg per day, preferably 0.2 to 10 mg/day, generally administered as a single dose, or as needed. Generally for treating respiratory diseases, a therapeutically effective amount will comprise the active ingredient in a quantity of from 0.02 to 15 mg/day, preferably 0.05 to 10 mg/day. The active ingredient may be given once a day. Preferably, however, the active ingredient will be administered in smaller doses two or three or more times a day to maintain more consistent plasma levels.

The Oxybutynin may be delivered in dry powder form, e.g. via a dry powder inhaler (DPI), metered dose inhaler (MDI), or dissolved in a suitable liquid for nebulization in a therapeutically effective unit dose delivery amount. For treating symptoms of stress urinary incontinence, a dose of Oxybutynin should be taken at the first sign of stress, or upon onset of the first sign of urgency or just prior to anticipated onset of stress, e.g. just before a patient is scheduled to talk in front of an audience. Similarly, for treating acute symptoms of respiratory distress, a dose of Oxybutynin should be taken at the first sign of respiratory distress. For treatment of chronic respiratory distress, Oxybutynin should be taken daily according to a regimen recommended by a physician. In a preferred embodiment of the invention, the dry powder Oxybutynin is packaged for delivery in a piezo-electronic dry powder inhaler such as described in U.S. Pat. No. 6,026,809.

Pulmonary delivery of Oxybutynin to the respiratory tract can be used advantageously to treat both urge urinary incontinence and symptoms of stress urinary incontinence. Unlike conventional oral and transdermal delivery of Oxybutynin which require chronic dosing with significant side effects and require hours to reach therapeutically active blood levels, dry powder pulmonary delivery of Oxybutynin permits a patient to enjoy relief at significantly lower doses with concomitant reduction in side effects such as dry mouth. Dry powder pulmonary delivery of Oxybutynin also permits a patient to enjoy relief from symptoms of stress urinary incontinence on an as-needed basis. Similarly, dry powder pulmonary delivery of Oxybutynin permits a patient to enjoy prophylactic relief from symptoms of respiratory distress or on an as needed basis.

A feature and advantage of the present invention that results from pulmonary delivery of Oxybutynin is that the typical primary metabolite formation of DEO is largely avoided as are the adverse side effects resulting therefrom as above mentioned.

Additionally, we have found that certain salts of Oxybutynin, when administered via pulmonary delivery result in a significantly longer acting efficacy effect than anticipated given that the oral half life is only 2.5 hours. These salts include not only the chloride salt but also a novel salt form of Oxybutynin, namely the xinafoate salt of Oxybutynin which heretofore has not been reported in the literature. For example, all dosing of Oxybutynin is typically three times daily due to a relatively short half-life of 2.5 hours with minimal plateau levels of drug remaining at approximately eight (8) hours. On the other hand, pulmonary delivery of a salt of Oxybutynin unexpectedly provides a duration of activity in guinea pig lungs of up to 18 hours which would translate into one to twice daily human dosing. This is illustrated in FIG. 1 attached.

The xinafoate salt of Oxybutynin is prepared by reacting Oxybutynin with xinafoic acid in methyl tert-butyl ether under an inert (nitrogen) atmosphere. Other salts of Oxybutynin that advantageously can be administered by pulmonary delivery include palmitate, pamoic, resinate, laurate and stearate salts and also esters of Oxybutnin, and provide unexpected results of improved half-life as well as reduced adverse metabolite production.

The following examples are provided to further illustrate the present invention:

Example 1

Oxybutynin in crystalline form is micronized to a median aerodynamic particle size of less than 10 microns. The powder is packaged in a dry powder inhaler (DPI) made in accordance with U.S. Pat. No. 6,026,809.

Example 2

Example 1 was repeated, using micronized Oxybutynin chloride of median aerodynamic particle size of less than 5 microns in place of Oxybutynin.

Example 3

Example 1 was repeated, using micronized Oxybutynin xinafoate salt of maximum aerodynamic particle size of about 10 microns in place of Oxybutynin. The Oxybutynin xinafoate salt was prepared by as follows: A 250 mL, round-bottom flask was equipped with a magnetic stirrer, a thermocouple, and a nitrogen-inlet adapter. Under nitrogen, the flask was charged with Oxybutynin (20.04 g, 0.056 mol.), xinafoic acid (10.69 g. 0.057 mol 1.02 equiv, and methyl tert-butyl ether (100 mL, 5 vol). The solids dissolved almost immediately at approximately 18° C. The batch was warmed to 50° C., and at approximately 21° C., crystallization started. The mixture was maintained at 50° C. for one hour, was cooled to 33° C. in air, and then in an ice bath to 3° C. The mixture was maintained at <5° C. for one hour and was filtered, and the filter cake was washed with methyl tert-butyl ether (100 mL). The wet cake was dried in a vacuum oven at 45° C. for one hour.

Example 4

Figure 2:
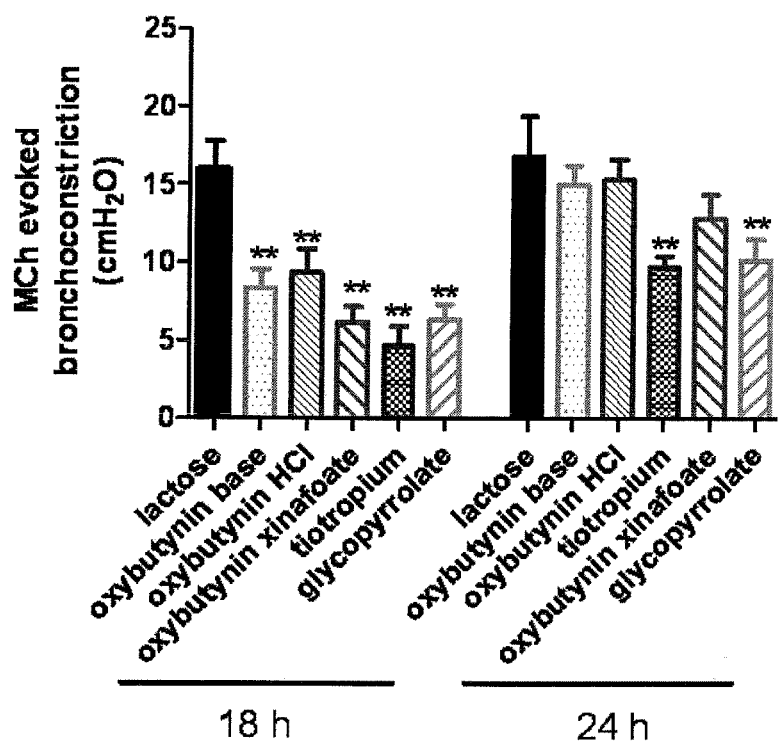
FIG. 2 compares inhibition of methacholine induced bronchoconstriction by Oxybutynin, Oxybutynin salts, tiotropium and glycopyrrolate at 18 hours and 24 hours.

Example 1 was repeated, using micronized Oxybutynin base, Oxybutynin hydrochloride salt, and Oxybutynin xinafoate salt of maximum aerodynamic particle size of about 10 microns in place of Oxybutynin. The level of bronchodilator activity of Oxybutynin was compared to Tiotropium and Glycopyrrolate 18 and 24 hours after administration in anaesthetized guinea pigs. FIGS. 1 and 2 shows comparative effects of pulmonary delivery of Oxybutynin on anaesthetized guinea pigs.

Example 5

Figure 3:
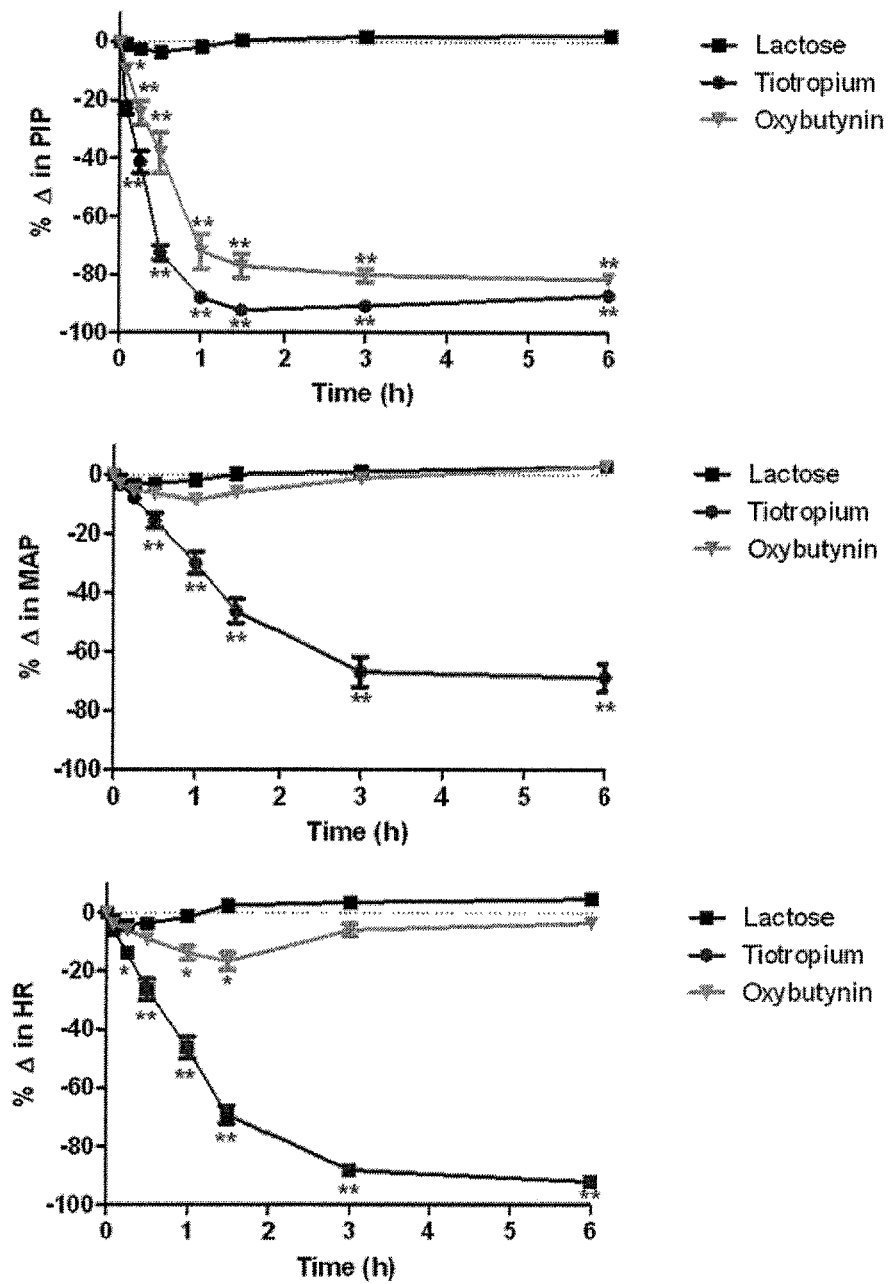
FIG. 3 is a series of graphs comparing changes from control response evoked by methacholine over time by Oxybutynin xinafoate and tiotropium in pulmonary inflation pressure, mean arterial blood pressure and heart rate.
Figure 4:
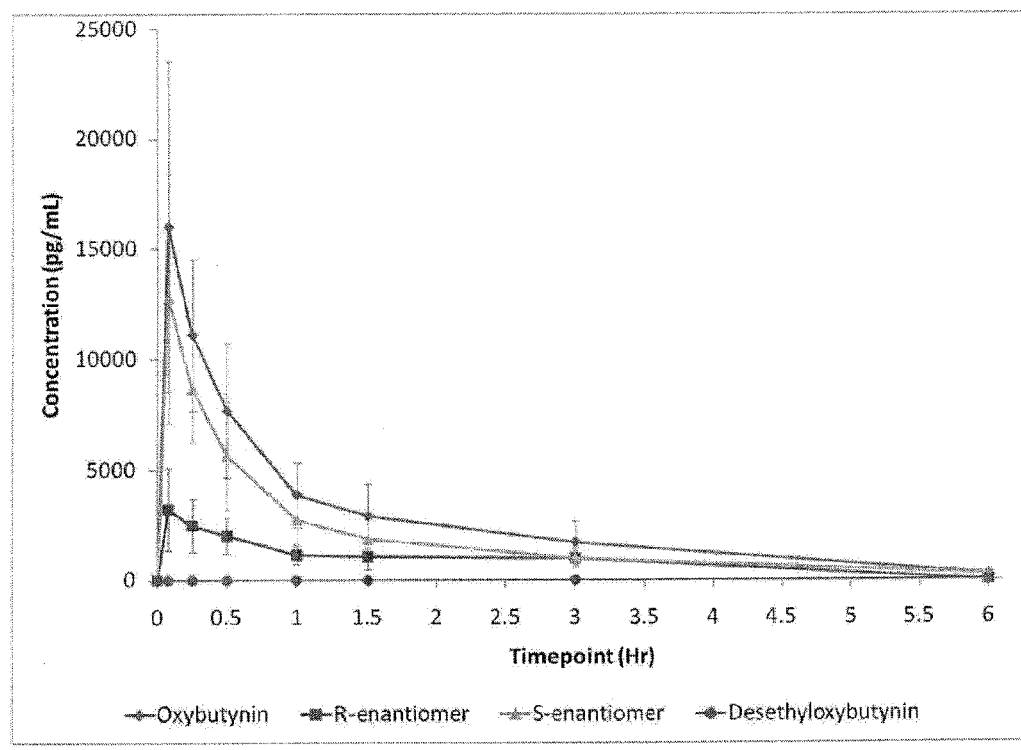
FIG. 4 shows pharmacokinetics of pulmonary administration of Oxybutynin over time.

Example 1 was repeated, using micronized Oxybutynin xinafoate salt of maximum aerodynamic particle size of about 10 microns in place of Oxybutynin. The onset of action and resulting systemic levels of Oxybutynin xinafoate was compared to Tiotropium for the first 6 hours after administration in anaesthetized guinea pigs. FIG. 3 compares effects of pulmonary delivery of Oxybutynin to Tiotropium on anaesthetized guinea pigs in the initial 6 hours after administration. Oxybutynin showed similar protection against methacholine induced airway constriction as Tiotropium; however, did not have as significant an influence on cardiovascular conditions. FIG. 4 shows the resulting pharmacokinetics of pulmonary administration of Oxybutynin. Systemic levels of DEO resulting from pulmonary delivery were below the LOQ of the detection method and much lower than clinically relevant levels Changes may be made without departing from the spirit and scope of the above-described invention. For example, the Oxybutynin may be co-administered with other compounds or agents for reducing adverse side effects or to treat the side effect. For example, cholinergic agonists such as described in PCT US09/034,018 may be co-administered with the Oxybutynin to reduce the effect of dry mouth.

CONCLUSION

Delivery of micronized particles of Oxybutynin directly to the lungs, as needed, could be found to provide relief to patients suffering from respiratory diseases such as asthma and COPD, and also from urge urinary incontinence and symptoms of stress urinary incontinence and irritable bowel syndrome.

In a guinea pig model of bronchoconstriction, Oxybutynin was found to have a significantly bronchoprotective effect from 0.25 to 24 hours without a prolonged significant effect on arterial pressure and heart rate.

Pulmonary administration of Oxybutynin also avoids significant formation of the first-pass primary metabolite DEO and thus significantly reduces adverse side effects which traditionally have been associated with administration of Oxybutynin via oral or transdermal delivery. Additionally, dosage amounts of Oxybutynin administered via pulmonary delivery route are significantly lower than dosage amounts of Oxybutynin when delivered via oral or transdermal delivery routes. Furthermore, pulmonary delivery of Oxybutynin results in prolonged therapeutic levels in the lungs which would permit once or twice daily dosing compared to oral delivery of Oxybutynin which typically is administered three times daily.

While the invention has been described in detail herein in accordance with certain preferred embodiments thereof, many modifications and changes therein may be affected by those skilled in the art. Accordingly, it is intended that the appended claims cover all such modifications and changes as may fall within the spirit and scope of the invention.

We claim:

1. A method for treatment of respiratory disease selected from the group consisting of asthma, chronic obstructive pulmonary disease, and pulmonary disease comprising delivering directly to a patient's lungs a therapeutically effective amount of an Oxybutynin xinafoate salt.

2. The method according to claim 1, wherein the Oxybutynin is delivered using a dry powder inhaler (DPI), a metered dose inhaler (MDI) or a liquid nebulizer.

3. The method according to claim 2, wherein the dry powder inhaler includes a piezo vibrator.

4. The method according to claim 1, wherein the dry powder Oxybutynin is delivered in dry powder form having a mass median aerodynamic particle size of 0.1-10 microns.

5. The method according to claim 1, wherein the dry powder Oxybutynin is delivered in dry powder form having a mass median aerodynamic particle size of 1-6 microns.

6. The method according to claim 1, wherein the therapeutically effective amount is within the range of 0.02 to 20 mg per day, administered as needed.

7. The method according to claim 6, wherein the therapeutically effective amount is within the range of 0.05 to 10 mg per day, administered as needed.

8. The method according to claim 1, wherein the therapeutically effective amount is within the range of 0.02 to 20 mg/day.

9. The method according to claim 8, wherein the therapeutically effective amount is within the range of 0.02 to 10 mg/day.

10. The method according to claim 1, wherein respiratory disease comprises asthma.

11. The method according to claim 1, wherein respiratory disease comprises chronic obstructive pulmonary disease.

12. The method according to claim 1, wherein respiratory disease comprises pulmonary disease.

\* \* \* \* \*